(12) United States Patent
Duffy et al.

(10) Patent No.: US 8,428,674 B2
(45) Date of Patent: Apr. 23, 2013

(54) APPARATUS FOR SPECTROMETRIC BASED OXIMETRY

(75) Inventors: Karen Duffy, Orange, CT (US); Douglas Pirc, Orange, CT (US); George Brocksieper, Guilford, CT (US); Paul B. Benni, Guilford, CT (US)

(73) Assignee: CAS Medical Systems, Inc., Branford, CT (US)

(*) Notice: Subject to any disclaimer, the term of this patent is extended or adjusted under 35 U.S.C. 154(b) by 1014 days.

(21) Appl. No.: 12/514,955

(22) PCT Filed: Nov. 14, 2007

(86) PCT No.: PCT/US2007/084665
§ 371 (c)(1),
(2), (4) Date: May 14, 2009

(87) PCT Pub. No.: WO2008/118216
PCT Pub. Date: Oct. 2, 2008

(65) Prior Publication Data
US 2010/0049018 A1 Feb. 25, 2010

Related U.S. Application Data

(60) Provisional application No. 60/865,761, filed on Nov. 14, 2006, provisional application No. 60/868,635, filed on Dec. 5, 2006.

(51) Int. Cl.
*A61B 5/1455* (2006.01)
(52) U.S. Cl.
USPC ............ 600/323; 600/310; 600/322; 600/336

(58) Field of Classification Search .................. 600/310, 600/322, 323, 324, 326, 340, 344, 473; 356/41
See application file for complete search history.

(56) References Cited

U.S. PATENT DOCUMENTS

| | | | |
|---|---|---|---|
| 5,217,013 A * | 6/1993 | Lewis et al. .................. 600/342 |
| 5,465,714 A | 11/1995 | Scheuing |
| 6,456,862 B2 | 9/2002 | Benni |
| 7,047,054 B2 | 5/2006 | Benni |
| 7,072,701 B2 | 7/2006 | Chen et al. |
| 7,190,986 B1 * | 3/2007 | Hannula et al. ............... 600/323 |
| 2002/0016536 A1 | 2/2002 | Benni |
| 2006/0189860 A1 | 8/2006 | Hacker et al. |
| 2006/0189861 A1 | 8/2006 | Chen et al. |
| 2006/0224053 A1 | 10/2006 | Black et al. |

FOREIGN PATENT DOCUMENTS
WO WO 2007/048039 4/2007

* cited by examiner

*Primary Examiner* — Eric Winakur
*Assistant Examiner* — Chu Chuan (JJ) Liu
(74) *Attorney, Agent, or Firm* — O'Shea Getz P.C.

(57) ABSTRACT

A spectrophotometric sensor assembly for non-invasive monitoring of a blood metabolite within a subject's body tissue is provided that includes a pad, a light source, and a light detector The light source is operative to emit light signals of a plurality of different wavelengths. The light detector is operative to detect light emitted by the light source and passed through the subject's body tissue. The light detector is at least partially enclosed in EMI shielding. In some embodiments, the light detector and EMI shielding are disposed in a detector housing that encloses the light detector and shielding. The housing is aligned with a detector aperture disposed in the pad.

26 Claims, 6 Drawing Sheets

APPARATUS FOR SPECTROMETRIC BASED OXIMETRY

This application is entitled to the benefit of, and incorporates by reference essential subject matter disclosed in PCT Application No. PCT/ US2007/084665 filed on Nov. 14, 2007, which claims priority to U.S. Provisional Patent Application No. 60/865,761 filed Nov. 14, 2006, and U.S. Provisional Patent Application No. 60/868,635 filed Dec. 5, 2006, the disclosures of which are herein incorporated by reference.

This invention was made with Government support under Contract No. 2R44NS45488-01 awarded by the Department of Health & Human Services. The Government has certain rights in the invention.

BACKGROUND OF THE INVENTION

1. Technical Field

This invention relates to methods and apparatus for non-invasively determining biological tissue oxygenation utilizing near-infrared spectroscopy (NIRS) techniques in general, and to sensors for use with such techniques in particular.

2. Background Information

Near-infrared spectroscopy is an optical spectrophotometric method that can be used to continuously monitor tissue oxygenation. The NIRS method is based on the principle that light in the near-infrared range (700 nm to 1,000 nm) can pass easily through skin, bone and other tissues where it encounters hemoglobin located mainly within micro-circulation passages; e.g., capillaries, arterioles, and venuoles. Hemoglobin exposed to light in the near- infrared range has specific absorption spectra that varies depending on its oxidation state; i.e., oxyhemoglobin ($HbO_2$) and deoxyhemoglobin (Hb) each act as a distinct chromophore. By using light sources that transmit near-infrared light at specific different wavelengths, and measuring changes in transmitted or reflected light attenuation, concentration changes of the oxyhemoglobin ($HbO_2$) and deoxyhemoglobin (Hb) can be monitored. The ability to continually monitor cerebral oxygenation levels, for example, is particularly valuable for those patients subject to a condition in which oxygenation levels in the brain may be compromised, leading to brain damage or death.

NIRS type sensors typically include at least one light source and one or more light detectors for detecting reflected or transmitted light. The light signal is created and sensed in cooperation with a NIRS system that includes a processor and an algorithm for processing signals and the data contained therein. U.S. Pat. No. 7,047,054 and PCT Published Application No. WO 07/048039, which are commonly assigned with the present application to CAS Medical Systems, Inc. of Branford, CT, disclose examples of such a sensor. Light sources such as light emitting diodes (LEDs) or laser diodes that produce light emissions in the wavelength range of 700-1000 nm are typically used. A photodiode or other light detector is used to detect light reflected from or passed through the tissue being examined. The NIRS System cooperates with the light source(s) and the light detectors to create, detect and analyze the signals in terms of their intensity and wave properties. U.S. Pat. Nos. 7,047,054 and 7,072,701, which are commonly assigned to CAS Medical Systems, Inc., of Branford, CT, disclose a methodology for analyzing such signals. U.S. Pat. No. 7,072,701, and PCT Published Application No. WO 07/048039are hereby incorporated by reference in their entirety.

Meaningful cerebral oxygenation information is collected from light interrogating brain tissue (e.g., passing through, reflecting from, absorbed by, etc.). To non-invasively access the brain tissue, however, the light signal must pass through extracerebral tissue (e.g., scalp, skull, etc.) before and after interrogating the brain tissue. A light signal traveling within any biological medium (e.g., tissue, fluid, etc.) will attenuate, and the amount of attenuation is a function of the medium. In the case of a mean optical path that non-invasively accesses brain tissue, the attenuation attributable to the extracerebral tissue does not yield useful information with respect to the cerebral oxygenation. Consequently, it is desirable to account for the signal attenuation attributable to extracerebral tissue, so that the attenuation attributable to the brain tissue can be distinguished and analyzed.

It is known to use a NIRS sensor having a pair of light detectors specifically spaced apart from a light source as a means to account for extracerebral tissue. A "near" light detector may be spaced apart from a light source by a first separation distance, and a "far" detector may be spaced apart from the light source by a second separation distance, which is typically greater than first separation distance. The method for spectrophotometric blood oxygenation monitoring disclosed within U.S. Pat. No. 7,072,701 is an example of a method that can be used with two detectors.

A problem common to all NIRS sensors is signal interference from ambient light sources, electromagnetic interference (EMI) sources, etc. Mitigating the effect of such interference improves the quality of the signal available, and therefore the patient information available. Another problem common to all NIRS sensors is the cost to manufacture. NIRS sensors are typically disposed of after use, so the cost of the sensor is an important factor in the cost of the monitoring.

What is needed, therefore, is an improved sensor for non-invasively determining the level of oxygen saturation within biological tissue, one that can be configured with one or more detectors, one that mitigates interference, and one that can be readily manufactured.

DISCLOSURE OF THE INVENTION

According to the present invention, a NIRS sensor assembly for non-invasive monitoring of blood oxygenation levels in a subject's body is provided. The sensor assembly comprises a pad, at least one light source, at least one light detector, at least one detector housing, and electromagnetic interference (EMI) shielding. The light source is operative to emit light signals of a plurality of different wavelengths, including those in the near-infrared range. The light detector is operative to detect light emitted by the light source and passed through the subject's body tissue. The shielding, which is disposed around at least a portion of the light detector, attenuates local EMI and thereby reduces undesirable noise within the light detector signals. The detector housing includes a base and a cap. The base includes a well sized to receive at least a portion of the light detector and shielding. The base and the cap mate to enclose the light detector and shielding. Alternatively, the shielding may be applied to interior surfaces of the detector housing. The housing is positioned relative to the pad so that the light detector is aligned with a detector aperture disposed in the pad.

An advantage of the present NIRS sensor assembly is the ease with which it may be manufactured. The detector housings enclose the light detectors and shielding and thereby increase the ease with which the shielding may be incorporated with the detectors. In addition, the detector housings help maintain the shielding in the desired position relative to the detectors.

Another advantage of the present NIRS sensor assembly is its flexibility and light weight. Patient skin surfaces can be complex, making it difficult to get optical sealing between the sensor and the patient surface. The independent detector housings of the present NIRS sensor assembly are lightweight and enable greater sensor flexibility than prior art devices using a solid spine, and yet maintain light source—light detector separation distances accurately.

The present NIRS sensor assembly is also cost effective relative to prior art sensors. The independent detector housings may be formed inexpensively, thereby obviating the relatively complex spine used in some sensor designs. As a result of this feature and others, the present NIRS sensor assembly is cost-effective.

These and other features and advantages of the present invention will become apparent in light of the drawings and detailed description of the present invention provided below.

DETAILED DESCRIPTION OF THE INVENTION

Figure 1:
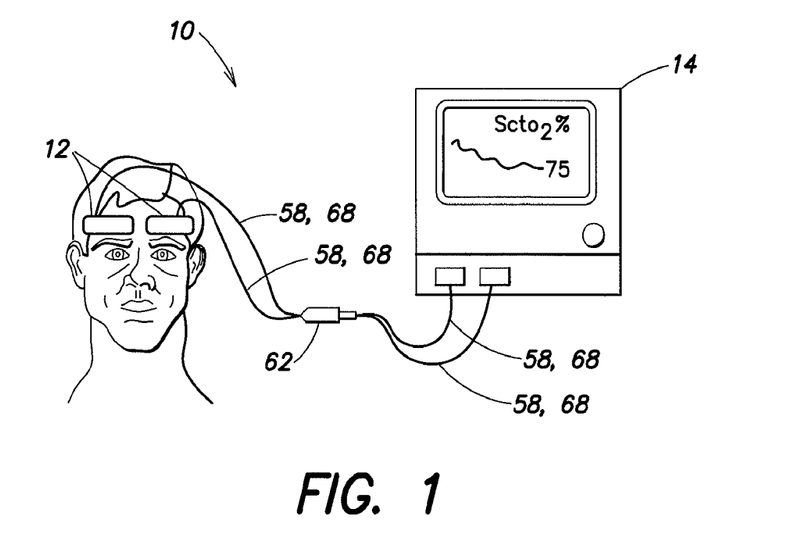
FIG. 1 is a diagrammatic view of a pair of NIRS sensor assemblies mounted on a patient and connected to a NIRS system.

Referring now to the drawings, a near infra-red spectroscopy (NIRS) system 10 includes one or more NIRS sensor assemblies 12 connected to a NIRS system 10. The NIRS system 10 includes a processor 14 for providing signals to and/or receiving signals from the NIRS sensor assembly (ies) 12. For purposes of providing a detailed description of the present NIRS sensor assembly 12, the sensor assembly 12 will be described herein as being used in connection with the NIRS system 10 described in U.S. Pat. No. 6,456,862 and U.S. Pat. No. 7,072,701,which are examples of acceptable NIRS systems. The NIRS sensor assembly 12 is not, however, limited to use with any particular NIRS system.

An embodiment of a NIRS sensor assembly 12 is shown in FIGS. 2-8. The NIRS sensor assembly 12 includes a pad 16, at least one light source 18, at least one light detector 20, at least one detector housing 22, electromagnetic interference (EMI) shielding 24, and a cover 26. In those embodiments of the present sensor assembly 12 that include more than one light detector 20, the present invention may include a plurality of detector housings 22.

Figure 2:
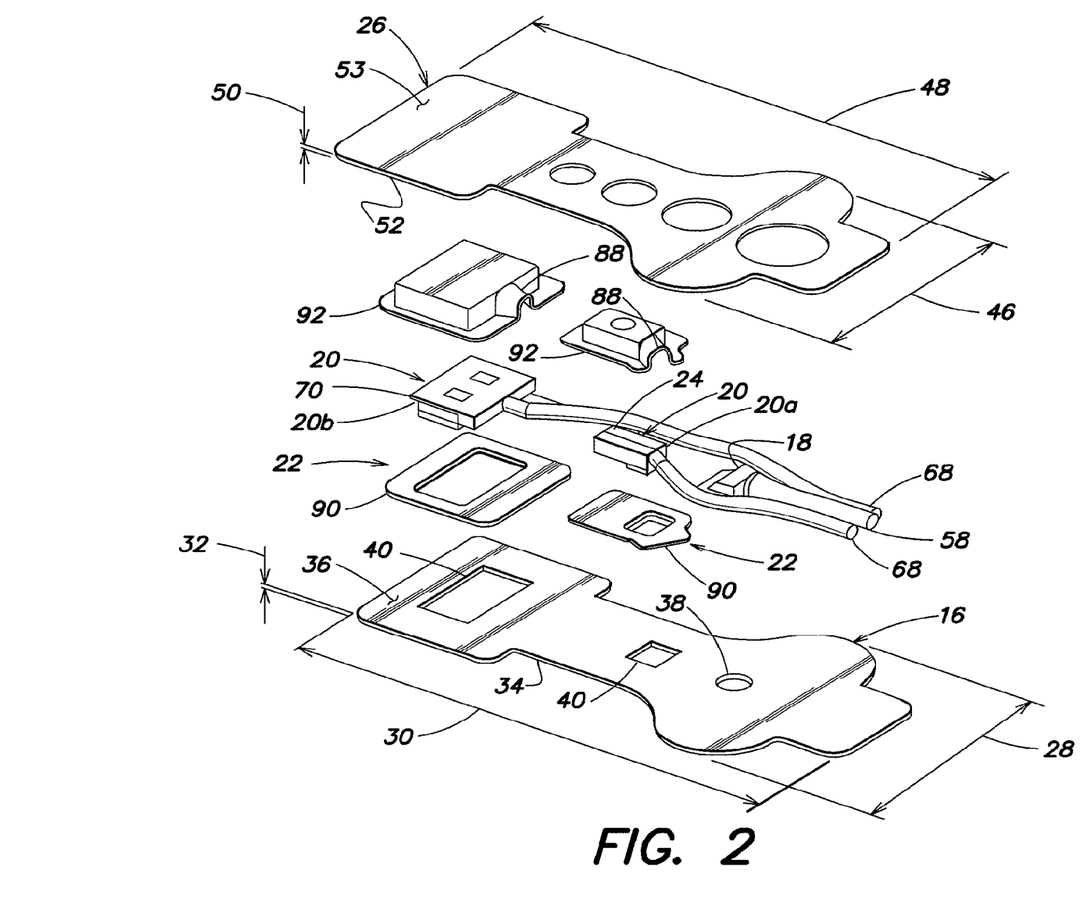
FIG. 2 is an exploded view of a NIRS sensor assembly.
Figure 3:
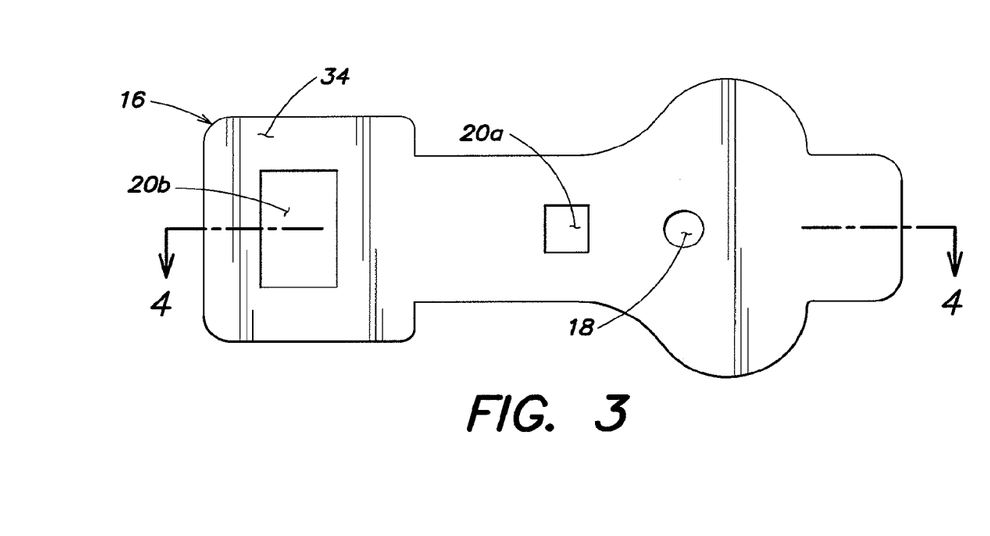
FIG. 3 is a diagrammatic planar view of a portion of a NIRS sensor assembly, illustrating the patient side surface of the pad.
Figure 4:
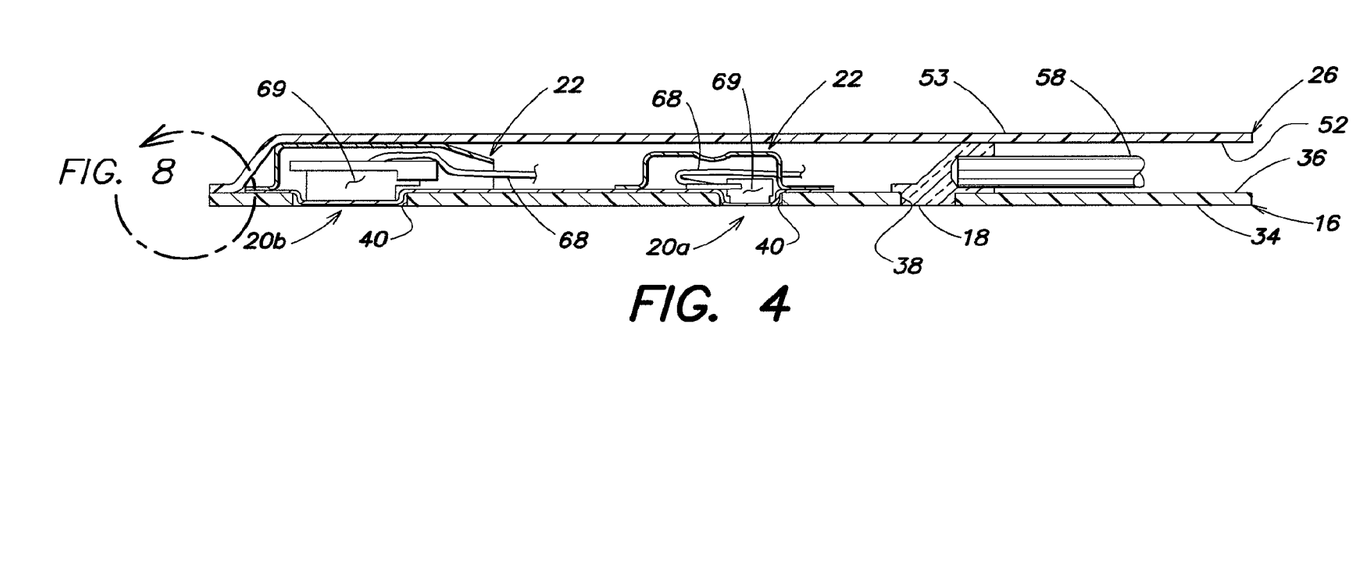
FIG. 4 is a sectional view of the NIRS sensor assembly portion shown in FIG. 3, sectioned along line 4-4.

Now referring to the embodiment shown in FIGS. 2 and 3, the pad 16 has a width 28, a length 30, a substantially uniform thickness 32, a patient side surface 34, a hardware side surface 36, at least one source aperture 38, and at least one detector aperture 40. The width 28 and length 30 are preferably contoured around one or both of the source aperture 38 and the detector aperture 40. In the embodiment shown in FIGS. 2 and 3, the pad 16 includes a pair of detector apertures 40 and a source aperture 38. The detector apertures 40 are each shaped to receive a portion of a detector housing 22, and the source aperture 38 is shaped to receive a portion of the light source 18. The detector and source apertures 40, 38 are typically aligned along a center line 42 of the pad 16. In some embodiments an adhesive 17 is applied to the patient side surface 34 for attaching the pad 16 to the patient (see FIG. 8). A removable protective layer 44 may be mounted on the adhesive covered patient side surface 34 to protect the adhesive until use. In some embodiments an adhesive is applied to the hardware side surface 36.

The pad 16 is preferably made from a flexible material (e.g., foam) that substantially or completely blocks the transmission of light energy through the pad 16. Poron® cellular urethane foam, a product of Rogers Corporation of Woodstock, Conn. USA, is an example of an acceptable pad 16 material.

In the embodiment shown in FIG. 2, the cover 26 has a geometry that matches the geometry of the pad 16. The cover 26 has a width 46, a length 48, a thickness 50, a hardware side surface 52, and an outer surface 53. The cover 26 may be made of a number of different materials, including the foam such as Poron® cellular urethane foam.

Figure 8:
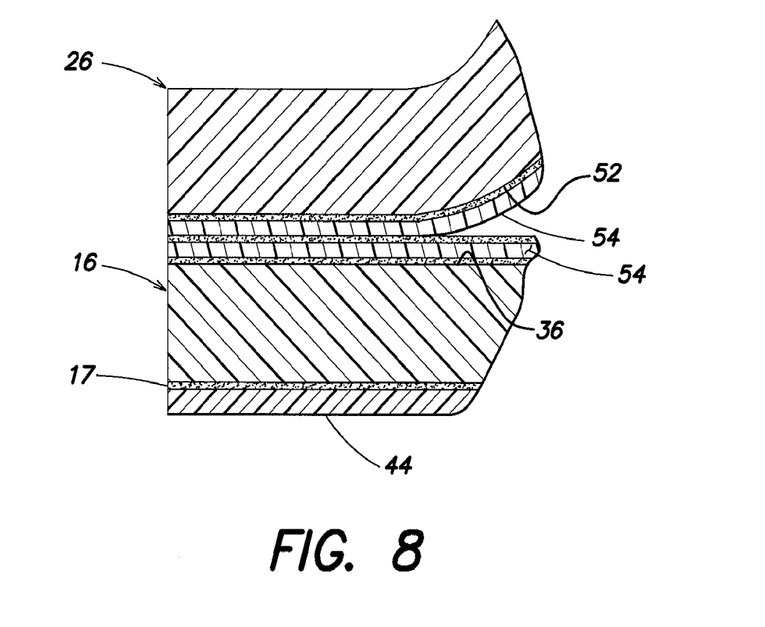
FIG. 8 is a sectional view of a portion of the sectional view shown in FIG. 4.
Figure 9:
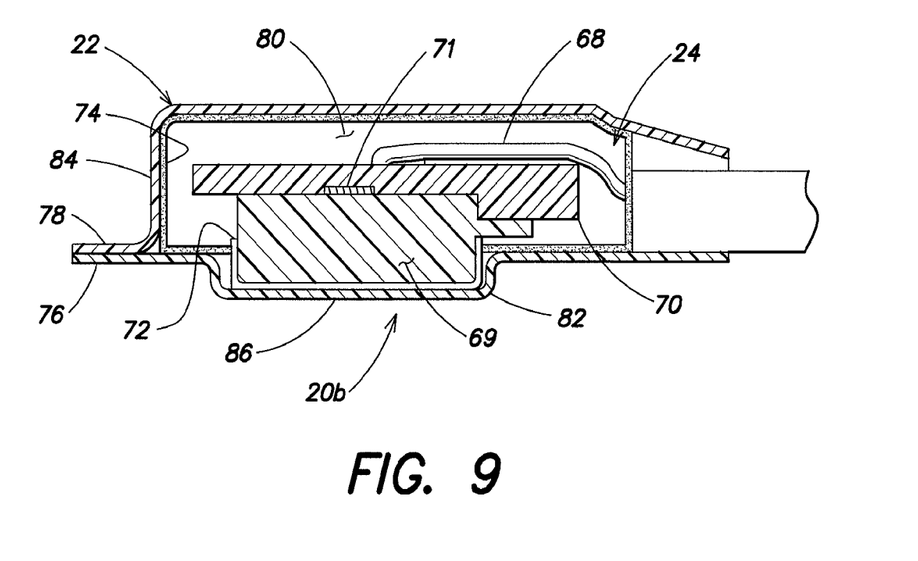
FIG. 9 is a sectional view of the detector housing shown in FIG. 4, illustrating an alternate shielding embodiment.

Referring to FIG. 8, one or more support layers 54 may be attached to one or both of the pad 16 and the cover 26. The support layer 54 is flexible, and may be described as having a width and a length oriented in similar direction as the width and length of the pad 16 and the cover 26. The support layer 54 resists stretching in the widthwise and/or lengthwise directions. Once a support layer 54 is attached to the pad 16 or to the cover 26, therefore, the support layer 54 resists stretching of the individual pad 16 or cover 26, and collectively the entire sensor assembly 12. An example of an acceptable support layer 54 material is Reemay® brand spunbonded polyester media, style no. 2006, offered by Reemay, Inc, of Charleston, S.C., USA. The present invention is not limited, however, to support layers 54 consisting of Reemay® brand spunbonded polyester media. In the embodiment shown in FIG. 8, a first support layer 54 is adhered to the hardware side surface 52 of the cover 26, and a second support layer 54 is adhered to the hardware side surface 36 of the pad 16.

The light source 18 is selectively operable to guide or emit infrared light (i.e., light in wavelength range of about 700 nm to about 1,000 nm). As stated above, infrared light provides particular utility in determining tissue oxygenation because hemoglobin exposed to light in the near-infrared range has specific absorption spectra that varies depending on its oxidation state; i.e., oxyhemoglobin ($HbO_2$) and deoxyhemoglobin (Hb) each act as a distinct chromophore. In alternative embodiments, however, there may be utility in examining blood metabolites that are best examined with a light outside the infrared range; e.g., in the visible light range between 400 nm and 700 nm, such as red light at 650 nm, or green light at 510 nm, or both visible and infrared light combinations, etc. In those applications, a light source may be utilized that emits or guides light outside the infrared range. In preferred embodiments, the light source 18 is an assembly that includes a fiber optic light guide 58 and a light redirecting prism 60. One end of the fiber optic guide 58 is optically connected to the prism 60. The other end of the fiber optic guide 58 is typically disposed within a connector 62 (see FIG. 1) that permits the fiber optic guide 58 to be optically coupled to fiber optic guide connected to the NIRS system 10. Other embodiments may have an optical fiber that is bent to create the proper alignment (e.g., bent ninety degrees (90°)). Examples of acceptable connector 62 embodiments are disclosed below. The fiber optic light guide 58 is diagrammatically shown in FIGS. 4 and 7 as a single fiber light guide. The fiber optic light guide 58 is not limited to a single fiber embodiment, and may comprise a plurality of fibers in alternative embodiments.

In the above-described preferred embodiments, the light source 18 does not create a light signal itself. Rather, a light signal or signals (collectively referred to hereinafter as a light signal) are introduced into the fiber optic guide 58 at a position external of the NIRS sensor assembly 12, and are guided into the sensor assembly 12 via the fiber optic guide 58. The present invention NIRS sensor assembly 12 is not limited to use with any particular method and/or apparatus for introducing a light signal into the fiber optic guide 58. U.S. Pat. No. 7,047,054, incorporated by reference hereinabove, discloses an acceptable example of an apparatus for introducing light energy into the fiber optic guide 58 that includes the use of laser diodes.

A light signal exits the fiber optic guide 58 and enters the prism 60 through an entrance face 64 and is redirected out of the prism 60 through an exit face 66. The fiber optic guide 58 can be connected to the entrance face 64 of the prism 60 in a variety of different ways. For example, the fiber optic guide 58 can be butted against the entrance face 64 of the prism 60 and held in place by a layer of clear epoxy disposed between the prism 60 and the fiber optic guide 58. In some embodiments, the prism 60 may be disposed within the NIRS sensor assembly 12 so that it will contact the patient's skin during use of the NIRS sensor assembly 12. The prism 60 is rigid so that when it is pressed against the patient's skin during the monitoring of blood oxygen, the surface of the skin is flattened, and the distance between the fiber optic guide 58 output and the skin surface via the prism 60 is constant across the entire illuminated area of the skin. This configuration controls the input light intensity and light illumination spot size on the skin, which is important in making accurate measurements.

Figure 7:
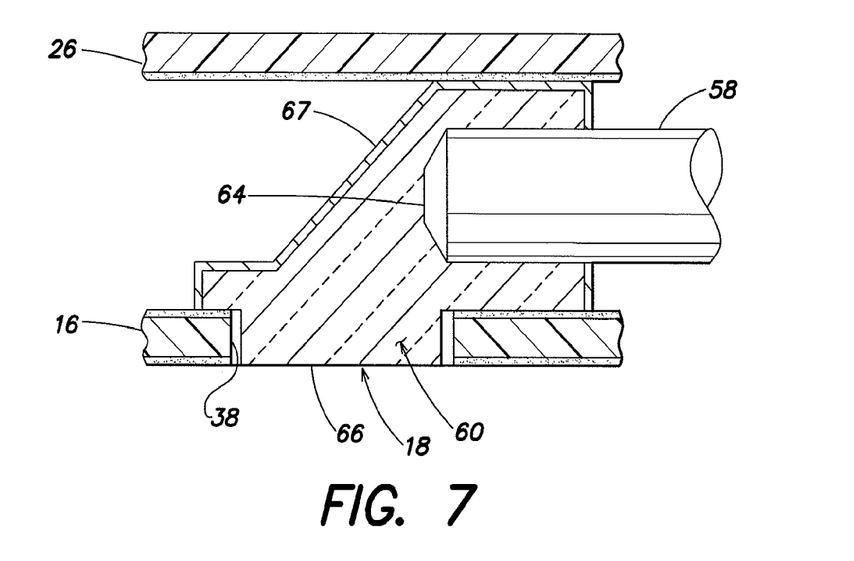
FIG. 7 is a sectional view of the light source shown in FIG. 4.

In the embodiment shown in FIG. 7, optical shielding 67 operable to at least partially impede the passage of light into or out of the prism 60 from a surface other than the entrance face 64 and exit face 66 is disposed around at least a portion of the prism 60. An example of an acceptable optical shielding 67 is a metal (e.g., copper) foil tape.

In alternative embodiments, the light source 18 may employ one or more LEDs mounted within the sensor assembly 12.

The light detector(s) 20 includes a light responsive transducer such as a photodiode that is operative to sense light intensity derived from light emitted by the light source 18 after such light passes through the subject's body. The light detectors 20 are electrically connected to the NIRS system to enable the output of the light detectors be communicated to the NIRS system 10. In a preferred embodiment, one or more EMI shielded cables 68 connect the light detectors 20 to the NIRS system 10. In the sensor embodiments having two light detectors 20, the light detector disposed closest to the light source 18 may be referred to as the "near detector 20a" and the other detector 20 disposed further away from the light source 18 as the "far detector 20b".

In the sensor embodiment shown in FIGS. 2-6, the far detector 20b includes a pair of photodiodes 69 mounted on a substrate 70 that includes a printed circuit board 71. The photodiodes 69 in the far detector 20b are electrically connected to the printed circuit board 71, and the printed circuit board, in turn, is electrically connected to the shielded cable 68. The near detector 20a includes a single photodiode 69 connected to the shielded cable 68. The number of photodiodes in one or both of the near and far detectors 20a, 20b may change to suit a particular application.

Figure 5:
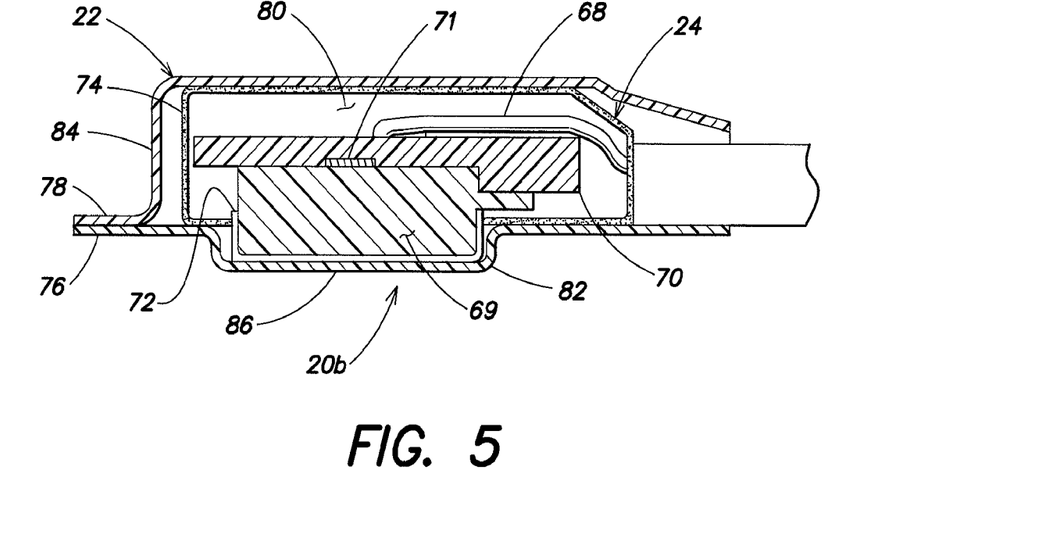
FIG. 5 is a sectional view of the detector housing shown in FIG. 4, containing the far detector.
Figure 6:
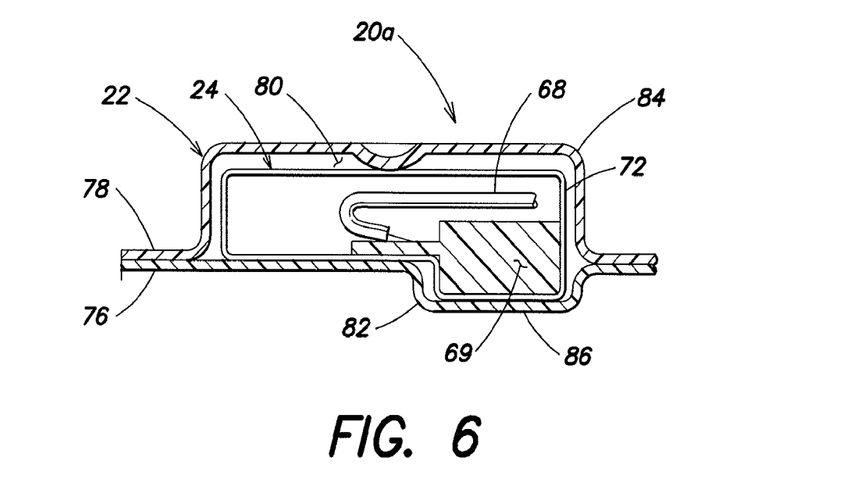
FIG. 6 is a sectional view of the detector housing shown in FIG. 4, containing the near detector.

FIGS. 5 and 6 illustrate EMI shielding 24 arrangements for the light detectors 20. The shielding 24 arrangement for the far detector 20b includes an optically transparent portion 72 and a non-transparent portion 74, the later disposed around substantially the entirety of the far detector 20b. For purposes of this description, the term "optically transparent" may be defined as follows: an optically transparent medium is one through which an amount of light may pass through, which amount is adequate for purposes of a NIRS evaluation. Conversely, an "optically non-transparent" medium is one that prevents passage of substantially all of light there through for purposes of a NIRS evaluation. The optically transparent portion 72 of the shielding 24 is disposed between the far light detector 20b and the patient's skin. The optically transparent portion 72 allows a percentage of the light signal produced by the light source 18 to be sensed by the far light detector 20b, after the light signal has traveled through the biological tissue of the patient. At the same time, the optically transparent portion 72 attenuates local EMI. Examples of acceptable optically transparent shielding 24 include, electrically conductive wire mesh (e.g., copper wire mesh), a thin optical member coated with an electrically conductive, optically transparent thin film on one side, etc. As will be explained below, the optically transparent portion 72 of the shielding 24 may be directly connected to ground, or indirectly connected to ground via the optically non-transparent portion 74 of the shielding 24 which is connected to ground.

The optically non-transparent shielding 24 portion may comprise an electro-conductive metal foil, such as a copper metal foil. The non-transparent shielding 24 portion typically surrounds the parts of the far detector 20b not utilized to sense light; e.g., the photodiode leads. An electrically conductive gasket, such as silicone paste, adhesive, foam, or other similar material, may be used to create an electrical interface between the optically transparent and optically non-transparent portions 72, 74 of the shielding 24.

The shielding 24 arrangement for the near detector 20a includes an optically transparent portion 72 similar or the same as that used with the far detector 20b; e.g., one that allows a percentage of the light signal produced by the light source 18 to be sensed by the near light detector 20a, after the light signal has traveled through the biological tissue of the patient. In the embodiment shown in FIG. 6, optically transparent shielding 24 is disposed around substantially the entirety of the near light detector 20a. In alternative embodiments, the shielding 24 for the near light detector 20a may include a non-transparent portion 74.

The above-described shielding 24 reduces undesirable EMI generated noise, and improves the signal to noise ratio of the light detectors 20 (e.g., photodiodes) by two different methods. First, the optically transparent shielding 24 creates a Faraday Cage around the light detector 20, while allowing light to reach the light-sensitive surface of the light detector 20. Second, as will be disclosed below, the detector housings 22 also create further EMI attenuation by increasing the light detector-to-biological tissue separation distance. The optically transparent spacer created by the detector housing 22 reduces the capacitance between the light detector 20 light sensitive surface and the biological tissue, such as human skin, resulting in an increased reduction in electromagnetic coupling and generated noise currents when compared to a sensor application that does not include such an optical spacer.

The detector housing 22 includes a base 76 and a cap 78 that together define an internal cavity 80, which cavity 80 is sized to enclose a light detector 20 at least partially covered with shielding 24 (and other materials as applicable). The base 76 and the cap 78 may be hinged together or they may be separable. The cap 78 includes a port 88 (see FIG. 2) for receiving a shielded cable 68. Alternatively, the port 88 may be partially disposed in both the base 76 and the cap 78, or solely in the base 76. The base 76 includes a well 82 sized to receive at least a portion of the light detector 20, and the cap 78 is sized to receive the remainder of the light detector 20 not received within the base well 82. The detector housing embodiments shown in FIGS. 2-6, for example, include a base 76 having a well 82 and a cap 78 having a well 84, which wells 82, 84 are sized to receive the light detector 20 in combination. In other embodiments, the base well 82 may be sized to receive the entire light detector 20 and shielding 24, and the cap 78 may be planar across the base well 82, or shaped to extend into the base well 82.

In some embodiments, the dimensions of the internal cavity 80 (i.e., height, width, depth) are such that there is a slight press fit between the light detector 20, shielding 24, etc. and the housing 22. As a result, the light detector 20 is positionally located and maintained within the housing 22. In alternative embodiments, the light detector 20 and shielding 24 may be positionally located and maintained within the internal cavity 80 by features (e.g., stems, ribs, etc.) integrally formed with the base 76 or cap 78, or elements disposed within the internal cavity 80 (e.g., a spacer, or biasing element), or by other means.

The base well 82 includes a window panel 86 that consists of an optically transparent material that allows light to pass there through and be sensed by the light detector 20. The window panel 86 may be a optically flat surface or it may be modified to focus or defocus detected light. The window panel 86 may also be treated to act as a filter with respect to chromaticity, wavelength, etc.

The base 76 and the cap 78 may be made out of the same material or different materials. In a preferred embodiment, the base 76 and cap 78 are formed from a material that has favorable dielectric characteristics (e.g., electrically insulative). The particular material, and therefore the dielectric characteristics, can be chosen to suit the application at hand. In addition, the amount of dielectric strength can also be chosen to affect the capacitance of a fixed geometry capacitor such as the window panel 86. As indicated above, the window panel 86 portion of the detector housing 22 increases the light detector-to-biological tissue separation distance, thereby reducing the capacitance between the light detector light sensitive surface and the biological tissue.

The base 76 and cap 78 engage and may attach to one another using adhesives, mechanical features (e.g., mating male/female pairs), welding, or the like. In the embodiment shown in FIGS. 2-6, the base 76 and cap 78 include mating flanges 90, 92 that attach to one another by an adhesive disposed on one or both of the flanges 90, 92. Each detector housing 22 is positioned so that at least a portion of the base well 82 is received within the respective detector aperture 40 of the pad 16. In the embodiment shown in FIGS. 2-6, the near light detector 20a and far light detector 20b are disposed within independent detector housings 22. In alternative embodiments, the bases 76 of the detector housings 22 may be connected to one another and/or the caps 78 of the detector housings 22 may be connected to one another.

The spacing between and the relative positioning of the near light detector 20a and the far light detector 20b within the sensor assembly 12 is preferably chosen so that: 1) the light source 18, near light detector 20a and the far light detector 20b are substantially linearly aligned with one another; and 2) the separation distance between the far light detector 20b and the near light detector 20a is greater than the separation distance between the light source 18 and the near light detector 20a. A greater distance between the near light detector 20a and the far light detector 20b (as compared to the separation distance between the light source 18 and the near light detector 20a) creates a significant difference between the region defined by the mean optical path extending between the light source 18 and near light detector 20a, and the region defined by the mean optical path extending between the light source 18 and the far light detector 20b. As a result, the information representing the contrast of the two signals is greater than it would be if the two mean optical paths were closer to one another.

The following examples illustrate light source 18/light detector 20 spacing for neonate, small adult/pediatric, and adult embodiments of the present sensor assembly 12. In an adult NIRS sensor assembly 12, the light source 18 may be positioned in the range of approximately forty-seven to fifty millimeters (47 mm to 50 mm) from the far light detector 20b and approximately fifteen millimeters (15 mm) from the near light detector 20a. In a small adult/pediatric embodiment of the NIRS sensor assembly 12, the light source 18 may be positioned in the range of approximately forty to forty-three millimeters (40 mm to 43 mm) from the far light detector 20b and approximately twelve millimeters (12 mm) from the near light detector 20a. In a neonate embodiment of the NIRS sensor assembly 12, the light source 18 is positioned in the range of approximately twenty-five to thirty millimeters (25 mm to 30 mm) from the far light detector 20b and approximately ten millimeters (10 mm) from the near light detector 20a. In an alternative neonate embodiment of the NIRS sensor assembly 12, the light source 18 may be positioned in the range of approximately twenty-five to thirty millimeters (25 mm to 30 mm) from a single light detector 20. The light source 18/detector 20 spacings described above represent examples and the present invention should not be construed to be limited to these examples.

In some embodiments, an EMI shielding material may be applied directly to the interior and/or exterior surfaces of the detector housing walls (e.g., wells, etc.) in addition to or in place of the shielding 24 that is disposed around the light detectors 20. The EMI shielding may be applied to only some detector wall surface, or a sufficient amount of detector wall surface so as to substantially surround the light detector disposed within the housing. The shielding may be applied by processes including printing, adhering, spraying, etc.

The cover 26 is shaped and positioned on the NIRS sensor assembly 12 so that the light source 18, the detector housings 22 containing the near and far light detectors 20a, 20b, and the shielded cable 68 are disposed between the cover 26 and the pad 16. The cover 26 preferably consists of a soft pliable material that can be used in a patient environment. Examples of acceptable cover materials include, but are not limited to, vinyl materials, plastic materials and foam materials (e.g., Poron®). The cover 26 may be attached to the NIRS sensor assembly 12 in a variety of different ways; e.g., by adhesive, mechanical features, etc. The cover 26 material preferably blocks light from entering the NIRS sensor assembly 12. The cover 26 may be molded, cast or formed in place over the sensor elements to create a tailored fit.

In preferred embodiments, the NIRS sensor assembly 12 includes a connector 62 that allows for attachment and removal of the sensor assembly 12 from the NIRS system 10. The connector 62 includes a fiber optic coupler and a shielded cable coupler. The fiber optic coupler provides an interface for optically connecting the fiber optics of the NIRS sensor assembly 12 to the NIRS system 10. Similarly, the shielded cable coupler provides an interface for connecting the photodiode output of the NIRS sensor assembly 12 to the NIRS system 10. In some embodiments, the connector 62 is a hybrid connector that incorporates the fiber optic coupler and the shielded cable coupler together into a single unit. In other embodiments, the connector 62 includes a fiber optic coupler and a shielded cable coupler that are independent of one another. In those embodiments where the fiber optic coupler and the shielded cable coupler are independent of one another, the two couplers may be located apart from one another; e.g., the fiber optic coupler at the sensor and the shielded cable coupler at a mid point.

In some embodiments, a photodiode preamplifier is used to amplify the light intensity signals derived from light emitted by the light source 18 that passes through the subject's body, and is sensed by the light detectors 20. The preamplifier may be disposed within the sensor assembly 12, connector 62, or NIRS system 10.

In some embodiments, a multi-fiber optic combiner may be used that allows for multiple laser light sources 18 of different wavelengths to be coupled into a small diameter core fiber optic output leading to the NIRS sensor assembly 12. The present invention sensor assembly 12 does not require the use of a multi-fiber optic coupler, and if one is used the present NIRS sensor assembly 12 is not limited to using any particular type or make of multi-fiber optic coupler. U.S. Pat. No. 7,047,054, which was earlier incorporated by reference into the present application, discloses an example of an acceptable multi-fiber optic coupler.

The connector 62 can also include sensor identification encoding means so that the NIRS system 10 can identify the type of NIRS sensor assembly 12 connected; i.e., an adult, pediatric, neonate, and other configured sensor. Once the type of sensor 12 is identified, the NIRS system 10 can then select appropriate information for use with that sensor 12; e.g., calibration information for a specific sensor configuration. Methods of encoding include but are not limited to: 1) setting different resistor values for each differently configured sensor 12 in which the NIRS system 10 can measure the resistance value though a voltage divider circuit; 2) incorporating a small memory device, such as a serial PROM, which has sensor identification information stored to be read by the NIRS system 10; and 3) including an RF identification device.

In the operation of the present invention, once the NIRS sensor assembly 12 is positioned relative to the subject's skin, the sensor may be actuated and near infrared light signals introduced into the subject's body tissue. The light introduced into the subject's body tissue is subsequently detected using the near and far light detectors 20a, 20b, producing signals representative of such detected light. The signals are relayed back to the NIRS system 10 via the shielded cable, where they are processed to obtain data relating to the blood oxygenation level of the subject's body tissue. As stated above, the present invention NIRS sensor assembly 12 is not limited to use with any particular NIRS system 10.

Since many changes and variations of the disclosed embodiment of the invention may be made without departing from the inventive concept, it is not intended to limit the invention otherwise than as required by the appended claims. For example, the present invention is disclosed in the context of a cerebral application. The present invention is not limited to cerebral oximetry applications and can be used for non-invasive monitoring of blood oxygenation levels in other body tissues and fluids.

What is claimed is:

1. A near infrared spectrophotometric sensor assembly for non-invasive monitoring of blood oxygenation levels in a subject's body tissue, said assembly comprising:
   a pad;
   at least one light source operative to emit light signals of a plurality of different wavelengths through a source aperture within the pad;
   at least one light detector operative to detect light emitted by the light source and passed through the subject's body tissue;
   electromagnetic interference shielding disposed around at least a portion of the light detector;
   a detector housing including a base and a cap, wherein the base includes a well sized to receive at least a portion of the light detector, and the cap is sized to receive a remainder of the light detector and shielding not received within the base well; and
   wherein the base and the cap mate to enclose the light detector and shielding, and the housing is positioned relative to the pad so that the light detector is aligned with a light detector aperture disposed within the pad;
   wherein the base includes a window comprising an optically transparent material that allows light to pass there through and be sensed by the light detector.

2. The sensor assembly of claim 1, wherein the cap includes a cap well sized to receive the remainder of the light detector and electromagnetic shielding not received within the base well.

3. The sensor assembly of claim 2, wherein the base and the cap attach to one another.

4. The sensor assembly of claim 3 wherein the cap is hingedly attached to the base.

5. The sensor assembly of claim 1 wherein the cap is hingedly attached to the base.

6. The sensor assembly of claim 1, wherein the detector housing further includes a port for receiving an electrical conductor.

7. The sensor assembly of claim 1, wherein the base is attached to the pad.

8. The sensor assembly of claim 1, wherein the cap is attached to the pad.

9. The sensor assembly of claim 1, wherein the detector housing has an interior cavity formed by the base and the cap, and wherein the light detector and electromagnetic shielding are positionally fixed within the interior cavity.

10. The sensor assembly of claim 9, wherein there is a press fit between the interior cavity and the light detector and electromagnetic shielding.

11. The sensor assembly of claim 1, wherein the electromagnetic shielding includes a solid shield disposed around at least a portion of the light detector.

12. The sensor assembly of claim 11, wherein the electromagnetic shielding further includes an optically transparent electromagnetic shielding disposed around at least a portion of the light detector.

13. The sensor assembly of claim 1, wherein the electromagnetic shielding further includes an optically transparent electromagnetic shielding disposed around at least a portion of the light detector.

14. The sensor assembly of claim 1, wherein the at least one light detector includes a first light detector and a second light detector, and each of said light detectors is disposed within a detector housing.

15. The sensor of claim 14, wherein the first detector includes at least one photodiode electrically connected to a printed circuit board.

16. The sensor of claim 1, further comprising a cover disposed over the light detector and the light source.

17. A spectrophotometric sensor assembly for non-invasive monitoring of a blood metabolite within a subject's body tissue, said assembly comprising:
- a pad having at least one source aperture and at least one detector aperture;
- at least one light source operative to emit light signals of a plurality of different wavelengths, the light source aligned with the source aperture;
- at least one light detector operative to detect light emitted by the light source and passed through the subject's body tissue;
- electromagnetic interference shielding disposed around at least a portion of the light detector;
- a detector housing including a first member and a second member, wherein the first member includes a well sized to receive a portion of the light detector and electromagnetic shielding, wherein the second member includes a well sized to receive a remainder of the light detector and electromagnetic shielding not received within the first member well; and
- wherein the first member and the second member mate to enclose the light detector and electromagnetic shielding, and the housing is positioned relative to the pad so that the light detector is aligned with the light detector aperture;
- wherein the first member includes a window comprising an optically transparent material that allows light to pass there through and be sensed by the light detector.

18. The sensor assembly of claim 17, wherein the light source is operative to emit light signals within the visible and/or near infrared range of 400 nm to 1000 nm.

19. The sensor assembly of claim 17, wherein the second member extends into the first member well.

20. The sensor assembly of claim 17, wherein the first member and second member are operable to attach to one another.

21. The sensor assembly of claim 20 wherein the second member is hingedly attached to the first member.

22. A near infrared spectrophotometric sensor assembly for non-invasive monitoring of blood oxygenation levels in a subject's body tissue, said assembly comprising:
- a pad;
- a light source operative to emit light signals of a plurality of different wavelengths through a source aperture in the pad;
- a light detector operative to detect light emitted by the light source and passed through the subject's body tissue, the light detector at least partially enclosed in EMI shielding, and the light detector and EMI shielding disposed in a detector housing having a base and a cap that mate to enclose the light detector and shielding wherein a portion of the light detector is received in each of the base and the cap, and the housing is aligned with a detector aperture in the pad;
- wherein the base includes a window comprising an optically transparent material that allows light to pass there through and be sensed by the light detector.

23. The sensor assembly of claim 22, wherein the housing comprises a dielectric material.

24. The sensor assembly of claim 22, wherein the detector housing base extends through the detector aperture and is positioned to permit the detector housing to contact the subject.

25. A near infrared spectrophotometric sensor assembly for non-invasive monitoring of blood oxygenation levels in a subject's body tissue, said assembly comprising:
- a pad having a source aperture, a first detector aperture, and a second detector aperture;
- a light source operative to emit light signals of a plurality of different wavelengths, the light source aligned with the source aperture;
- a first light detector at least partially enclosed in EMI shielding, and the first light detector and EMI shielding enclosed within a first detector housing, and the first detector housing is positioned relative to the pad so that the first light detector is aligned with the first detector aperture; and
- a second light detector at least partially enclosed in EMI shielding, and the second light detector and EMI shielding enclosed within a second detector housing, and the second detector housing is positioned relative to the pad so that second light detector is aligned with the second detector aperture;
- wherein at least one of the first detector housing and the second detector housing includes a window comprising an optically transparent material that allows light to pass there through and be sensed by the respective light detector and a base and a cap each receives a portion of the respective light detector.

26. The sensor assembly of claim 25, wherein the first detector housing and the second detector housing are independent of one another.

* * * * *